(12) United States Patent
Gramer et al.

(10) Patent No.: US 6,590,403 B1
(45) Date of Patent: Jul. 8, 2003

(54) MATERIAL REGRESSION SENSOR

(75) Inventors: Daniel J. Gramer, Madison, WI (US); Thomas J. Taagen, Belleville, WI (US)

(73) Assignee: Orbital Technologies Corporation, Madison, WI (US)

( * ) Notice: Subject to any disclaimer, the term of this patent is extended or adjusted under 35 U.S.C. 154(b) by 0 days.

(21) Appl. No.: 09/832,471

(22) Filed: Apr. 11, 2001

Related U.S. Application Data
(60) Provisional application No. 60/197,493, filed on Apr. 17, 2000, and provisional application No. 60/198,078, filed on Apr. 17, 2000.

(51) Int. Cl.[7] .................. G01R 27/08; G01N 27/00; H01C 3/04
(52) U.S. Cl. .................. 324/716; 324/71.2; 324/700; 338/25; 338/28
(58) Field of Search .................. 324/716, 700, 324/691, 693, 721, 724, 71.2; 338/28, 25; 374/185

(56) References Cited

U.S. PATENT DOCUMENTS

| | | | | |
|---|---|---|---|---|
| 3,844,832 A | * | 10/1974 | Gabrusenok | 236/44 E |
| 3,898,730 A | * | 8/1975 | Haraway et al. | 29/610.1 |
| 4,420,974 A | * | 12/1983 | Lord | 338/25 |
| 5,158,366 A | * | 10/1992 | Nagai et al. | 338/28 |
| 5,977,782 A | * | 11/1999 | Kordecki | 324/700 |
| 6,208,128 B1 | * | 3/2001 | Braconnier et al. | 324/700 |

OTHER PUBLICATIONS

B.B. McWhorter, et al.; "An Instrument for Real–Time Measurement of Solid Rocket Motor Insulation Erosion", *American Institute of Aeronautics and Astronautics*, 1999, pp. 1–6.

U. Carretta et al.; "Scope of Capacitive Methods in Solid Propellant Diagnostics", *Journal of Propulsion and Power*, vol. 15, No. 6. 1999, pp. 849–855.

* cited by examiner

*Primary Examiner*—N. Le
*Assistant Examiner*—Anjan K. Deb
(74) *Attorney, Agent, or Firm*—Dorsey & Whitney LLP

(57) ABSTRACT

A material regression sensor and a method of measuring the regression of a material in which the regression sensor includes spaced electrically conductive legs, and electrically conductive sensor element position between the legs and measurement leads electrically connected with the first and second legs.

25 Claims, 9 Drawing Sheets

MATERIAL REGRESSION SENSOR

This application claims the benefit of Provisional Application Serial No. 60/197,493 filed Apr. 17, 2000 and Provisional Application Serial No. 60/198,078 filed Apr. 17, 2000.

BACKGROUND OF THE INVENTION

1. Field of the Art

The present invention relates generally to a material regression sensor and more particularly to an electrically resistive surface regression and ablation sensor for detecting and continuously measuring the instantaneous surface regression in materials. The invention has particular applicability for measuring instantaneous surface regression in hybrid rocket solid fuels and solid oxidizers, solid rocket propellants, ablative rocket nozzles, thermal protection materials, and other subliming, melting, wearing, or ablating materials. The invention also relates to a method of measuring such instantaneous surface regression. Regression in this case is defined as the dimensional loss of material from the surface of objects in question.

2. Description of the Prior Art

A long-standing need exists in the rocket propulsion community for an accurate, low cost, and reliable means of measuring surface regression in solid propellants, hybrid rocket solid fuel and solid oxidizer grains, ablative nozzles, thermal protection materials, and other materials. Two publications describe work by others to address this need.

A first publication entitled *An Instrument for Real Time Measurement of Solid Rocket Motor Insulation Erosion* was published at the 35$^{th}$ AIAA/ASME/SAE/ASEE Joint Propulsion Conference and Exhibit on Jun. 20–24, 1999. This publication discloses a pair of twisted wires which are polyimide insulated. The twisted wires are mounted in the motor insulation in a position in which the tip of the wires will recede with the erosion of the rocket motor internal insulation. As the combustion proceeds, the tips of the wires are melted to provide a completed circuit. A constant current applied along the wires will detect the resistance change via a voltage drop across the wires as the wire pair recedes with the decomposition of the insulation. This sensor is designed for a specific type of material and relies on the presence of a combustion process to melt the wires and thereby complete the electrical circuit. A problem with this particular sensor is that it may tend to disrupt or otherwise adversely effect the burning of hybrid fuels and solid propellants, thereby resulting in an uneven combustion surface. Another issue with this concept is that the location of the twisted wire tip within the host material is dependent upon the host material properties. A further issue with this concept is that it has been shown to be unreliable in certain materials.

A second publication entitled *Scope of Capacitive Methods in Solid Propellant Diagnostics* was published in the *Journal of Propulsion and Power*, Vol. 15, No. 6, November–December 1999. This publication disclosed an apparatus for instantaneous regression rate measurement of solid rocket propellants. The sensor of this publication is based on measuring capacitance, not resistance. Further, the concept of this sensor uses the host material, the propellant whose regression is being measured, as an active portion of the sensor. This adversely effects the reliability of the sensor and limits its applicability to unmetalized propellants. Additionally, this concept requires accurate knowledge of the solid propellant capacitance, which may vary from batch to batch, and thus, require calibration for each propellant batch. A further limitation of this concept is that substantial analytical correction factors must be applied to the results to account for electrical noise derived from combustion of the solid propellant.

Approaches utilizing ultrasonic and X-ray technologies have also been considered for measuring surface regression. Ultrasonic systems emit a pulse of sound at one side of the host material and measure the time it takes for the pulse of sound to travel through the material, or alternatively, the time it takes for the pulse to reflect off of the other surface of the material and return to the point of origin. Correlating this travel time with the speed of sound in the host material allows a calculation of the instantaneous material thickness. X-ray systems function by passing X-rays through the host material and measuring the attenuated X-ray intensity on the other side. The spatial intensity of the signal can be reduced to arrive at the material thickness as a function of time. Both ultrasonic and X-ray systems can provide accurate regression data, however, they require exceedingly high investments in personnel training and hardware, and also require in-situ calibration. Additionally, both X-ray and ultrasonic systems are not well suited for use onboard flight systems due to their relatively large size, high mass, and high power requirements.

Accordingly, there is a need in the art for a low-cost material regression sensor and more particularly to a material regression sensor which can accurately, reliably, continuously, and instantaneously measure the regression rate of materials, and in particular, of solid fuel or oxidizer hybrid rocket grains, solid rocket propellants, and other materials.

SUMMARY OF THE INVENTION

The present invention relates to a resistive regression and ablation sensor which can accurately, reliably and affordably measure surface regression, and acquire the data as a function of time. The sensor of the present invention can accurately measure the time dependent regression, ablation, or wear rate of a material, and thus eliminate the need to conduct multiple tests or make multiple measurements to determine the ☐instantaneous☐ dimensions of the material being monitored. Additionally, the sensor does not require any end user calibration or personnel training.

In general, the sensor of the present invention includes an electrically conductive, but high resistivity, sensor layer applied to a substrate and a means for applying a current (or voltage) to such sensor layer and measuring the voltage drop (or current) across the layer. Preferably, the sensor layer is embedded within the test material whose regression is desired to be measured with a first end at or near the regressing surface, and perpendicular thereto, and a second end connected with a pair of measurement leads. The sensor layer is embedded in the material such that as the material regresses, the length of the sensor shortens. Because the resistance of the sensor layer is related to its length, the amount which the material surface regresses can be instantaneously and continuously measured by applying a current (or voltage) to the measurement leads and measuring the voltage drop (or current) across the sensor layer.

More specifically, the surface regression sensor of the present invention includes an elongated, non-conductive substrate and first and second electrically conductive legs applied to the substrate and extending from a measurement end to a free end of the sensor. The legs are spaced from one another and are preferably parallel to one another. The electrically conductive, high resistivity sensor layer is applied to the substrate between the conductive legs and is electrically connected to the legs. Preferably, the conductive legs are of a relatively low resistivity material, while the sensor layer is of a relatively high resistivity material. The sensor layer and conductive legs in the preferred embodiment are a thin film, conductive ink, or other electrically conductive material.

First and second measurement leads are electrically connected with measurement ends of the conductive legs, and the sensor is embedded in the material whose regression is to be measured by positioning the free end of the sensor at the regression surface. By applying a current (or voltage) to the measurement leads and measuring the voltage drop (or current) across the sensor layer, the instantaneous thickness and regression rate of the test material can be determined.

The method aspect of the present invention relates to a method of measuring the regression of a material having a regressing surface. The phenomena causing the regression of the surface may include, but is not limited to, abrasive or other wearing, melting, ablation, sublimation, and combustion. Specifically, the method includes providing a sensor with a pair of spaced electrically conductive legs, an electrically conductive sensor layer extending between the legs and a pair of measurement leads electrically connected to the pair of legs. The method further includes embedding the sensor in the material whose regression measurement is desired with one end of the legs extending to the regression surface. Alternatively, the sensor can be installed behind the regression surface but will not detect or begin regression measurement until the surface has regressed to the test end of the sensor. Finally, the method includes applying a measurement current (or voltage) to the measurement leads and measuring the voltage drop (or current) and thus the resistance across the legs and the conductive sensor layer and from that information determining the extent of material regression.

Accordingly, it is an object of the present invention to provide a material regression sensor which can accurately and reliably detect and measure surface regression in a material.

Another object of the present invention is to provide a sensor for continuously measuring the instantaneous regression of a hybrid rocket fuel grain, solid rocket propellant, ablative, or other material.

A further object of the present invention is to provide a miniature resistive regression sensor for a hybrid rocket fuel grain, solid rocket propellant, ablative, or other material.

A still further object of the present invention is to provide a method for continuously and instantaneously measuring the regression of a hybrid rocket fuel grain, solid rocket propellant, ablative, or other material.

These and other objects of the present invention will become apparent with reference to the drawings, the description of the preferred embodiment and the appended claims.

DESCRIPTION OF THE PREFERRED EMBODIMENT

The regression sensor of the present invention has a variety of applications including the ability to instantaneously measure the surface regression of a hybrid rocket fuel or oxidizer grain, solid rocket propellant grain, ablative rocket nozzle or thermal protection material, thereby facilitating the development and testing of hybrid fuels, solid propellants, rocket nozzles, and thermal protection materials. The sensor of the present invention also has applicability for use in onboard flight systems, providing a feedback signal to allow tighter control and health monitoring of the vehicle and motors. The sensor of the present invention has still further applicability to measure the surface regression of any material, including automobile tires and brake pads, among others. Although there are a wide variety of applications for the sensor of the present invention, it has particular applicability as a regression sensor for solid rocket fuels and propellants, and accordingly, the preferred embodiment will be described with respect to such application.

Figure 1:
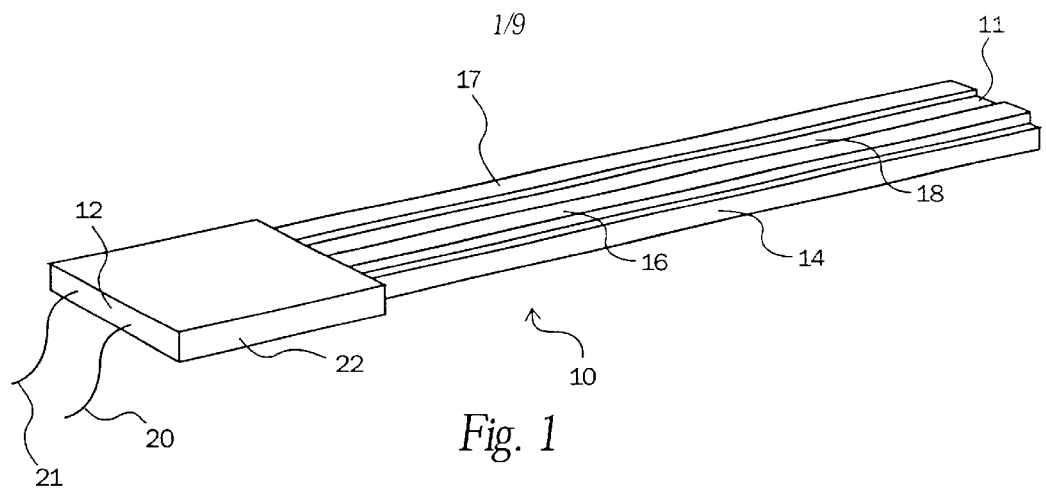
FIG. 1 is an isometric view of a regression sensor with a continuous sensor layer pattern in accordance with the present invention.

Several sensor patterns and configurations, including ladder and continuous, are described below. With reference to FIG. 1, the sensor 10 of the preferred embodiment for the continuous sensor pattern is comprised of an elongated structure having a first or test or regression end 11 and a second or measurement end 12. As will be described in greater detail below, the sensor 10 is designed to be cast into the test material whose regression is desired to be measured or to be otherwise inserted into the test material after it has been formed or cast. When installed, the test end 11 is usually at or closely adjacent to the regressing surface of the test material whose regression is desired to be measured. Alternatively, the sensor can be installed behind the regression surface but will not detect or begin regression measurement until the surface has regressed to the test end 11 of the sensor.

Figure 2:
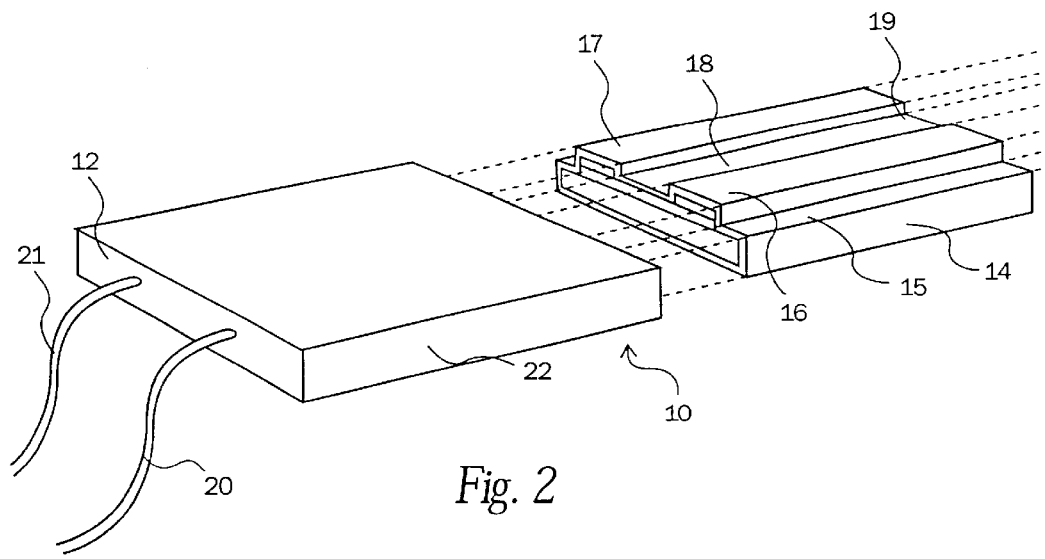
FIG. 2 is an enlarged, fragmentary view of the measurement end of the sensor with the continuous sensor layer pattern of the present invention.

With continuing reference to FIG. 1 and further reference to FIG. 2, this embodiment of the sensor 10 includes a structural substrate 14 of electrically insulating material extending the entire length of the sensor. Although the substrate 14 in the embodiments of FIGS. 1 and 2 is shown as having a generally rectangular configuration, it can be any shape. The substrate 14 includes a first sensor support surface 15 and a second or opposite surface (not shown).

Figure 3:
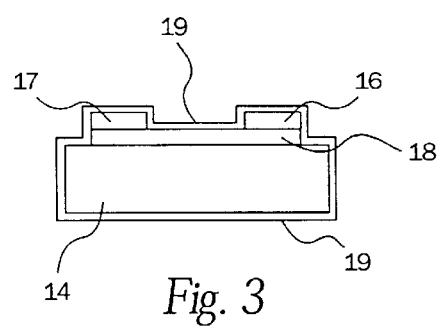
FIG. 3 is a sectional view as viewed along the section line 3—3 of FIG. 2.

A pair of relatively low resistivity, electrically conductive legs 16 and 17 are applied to the insulating substrate 14 or, as described below, onto a previously applied sensor coating or layer 18. The legs 16 and 17 preferably extend the entire length of the substrate and are equally spaced from one another along their length, although if desired, the distance between the legs can vary. Positioned between the legs 16 and 17 and in electrical engagement therewith is an electrically conductive, high resistivity sensor element in the form of a coating or layer 18. The sensor layer 18 is applied to the substrate 14 and extends between the legs 16 and 17 and along the entire length of the legs 16 and 17 and thus preferably the substrate 14. An electrically insulating coating 19 can be applied over the sensor layer 18 and the legs 16 and 17, if desired, to insulate such elements from the test material whose regression is being measured. Also, if desired, the entire assembly comprised of the substrate, sensor coating, and legs can be coated with the electrically insulating coating to provide better adhesion between the host or test material under study and the sensor. FIG. 3 shows the insulating coating 19 applied over the entire sensor. A pair of conductive leads 20 and 21 are electrically connected, respectively, to the legs 16 and 17 at the measurement end of the sensor. The connection of the leads 20 and 21 can be facilitated through the use of a crimp type connector 22 which mechanically clamps onto the legs 16 and 17. Other methods of lead attachment are equally viable including the use of ultrasonic welding, parallel gap welding, solder, and conductive adhesives and epoxies.

Figure 4:
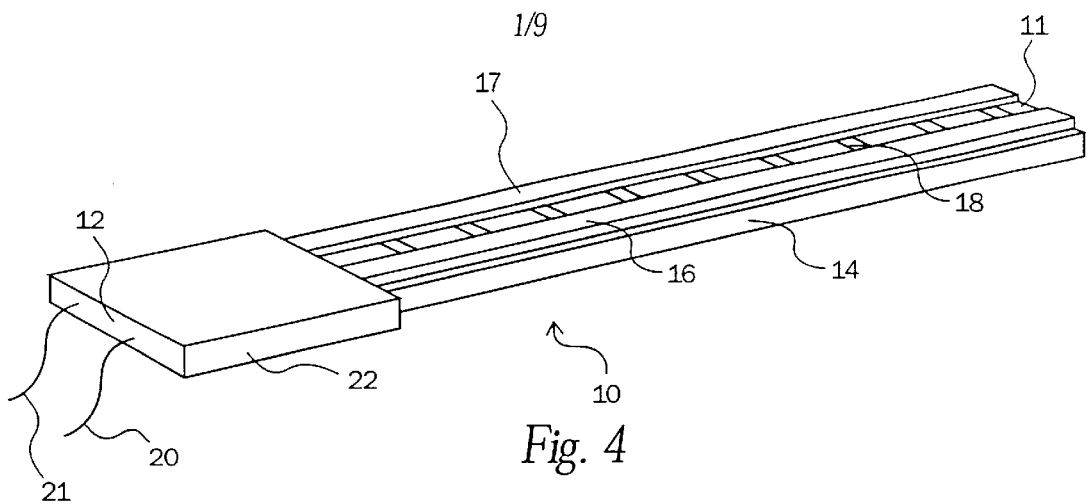
FIG. 4 is an isometric view of a regression sensor with a ladder sensor layer pattern in accordance with the present invention.
Figure 5:
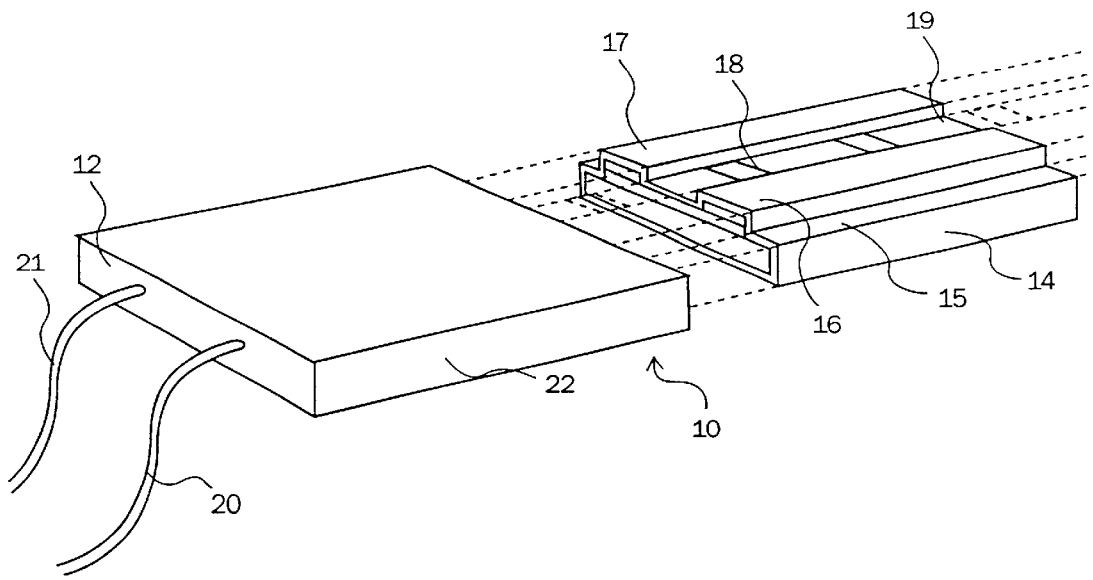
FIG. 5 is an enlarged, fragmentary view of the measurement end of the sensor with the ladder sensor layer pattern of the present invention.

FIGS. 4 and 5 show an alternate high resistivity element 23 in a pattern referred to as the ladder pattern. Like the embodiment of FIGS. 1–3, the sensor 10 of FIGS. 4 and 5 includes an electrically insulative substrate 14 and a pair of spaced electrically conductive legs 16 and 17. However, instead of the continuous sensor layer 18 of FIGS. 1–3, the embodiment of FIGS. 4 and 5 includes a center resistive coating comprised of several individual electrically conductive, high resistivity strips or conductive element portions 23, sometimes called rungs 23, between and in electrical contact with the conductive legs 16 and 17. Electrically, the sensor pattern of the ladder embodiment is equivalent to several resistors in parallel. As shown, the plurality of high resistivity conductive portions 23 are spaced along the longitudinal axis or length of the sensor. The width and spacing of the individual rungs 23 can vary. The other features of the ladder sensor are otherwise similar to the continuous sensor, shown in FIGS. 1–3.

The ladder pattern sensor has particular application where there are several potential sources of sensor disturbance during use such as heat conduction, combustion of the sensor tip, shorting across the sensor tip, and electrical noise derived from the combustion process. With some applications, these disturbances diminish the performance of the continuous sensor design to the point where it is difficult to distinguish between noise and physical measurements. The ladder sensor design addresses this problem by providing discrete changes (jumps) in resistance as each rung 23 of the ladder is burned or worn away. These changes are designed to be larger than the background noise. By comparing the timing of these jumps in resistance and the spacing of the rungs, the surface regression of the host material can be determined. Additionally, applying a curve fit to the data (length vs. time) and then integrating the curve fit with respect to time can provide an accurate estimation of the instantaneous surface regression rate for periods where the surface regression is between two rungs 23. Resolution can be improved by decreasing the spacing between the rungs 23.

Although the specific material from which the various components of the sensor are constructed can vary, the preferred materials include those that are compatible with one another and, when formed together into a sensor as described above, function to provide the desired goal of accurately, reliably, and repeatedly measuring the instantaneous surface regression without disrupting the regression process or the process under consideration.

The substrate material should preferably be of a material to withstand the application temperatures and environment of the resistive elements 16, 17, 18 and 23. Further, the substrate material should preferably burn at approximately the same temperature and rate as the test material, and should not disrupt the regression of the test material. Substrate materials which burn substantially hotter and slower than the test material have the potential to create problems. Specifically, in such a situation, as the test material regresses, the unburned substrate protrudes into the chamber and creates recirculation zones resulting in greatly accelerated material regression in the regions around the substrate. This problem is compounded by thicker substrates. Thus, it is desirable for the substrate 14 to also be as thin as possible, while still functioning to support the resistive elements 18 and 23 and the legs 16 and 17. Further, it is preferable for the substrate material to remain electrically non-conductive when it burns or chars to prevent undesirable electrical shorts between the conductive legs 16 and 17.

In the preferred embodiment for measuring the regression of a hybrid rocket fuel grain, the preferred substrate is comprised of polyester or celluloid. In the preferred embodiment for measuring the regression of a composite solid rocket propellant grain, the preferred substrate is comprised of celluloid. These substrates are preferably on the order of less than 0.010 inches thick, although other thicknesses will work as well. Other possible substrate materials may include alumina, fiberglass, mica, phenolic and acrylic, among others. As indicated above, the selection of the specific substrate material is to some extent dependant upon the specific host material whose surface regression is to be measured. The electrically conductive legs 16 and 17 may comprise any material that has a high electrical conductivity relative to the conductivity of the sensor elements 18 and 23, can be applied to the mating substrate material 14 without damaging it, and will not disrupt the process understudy. Preferably, the conductive legs 16 and 17 are comprised of thin films of copper or electrically conductive ink which are deposited directly onto the high resistive coating 18 or 23, which has been previously applied. Other materials may also be used for the conductive legs, including conductive paints, adhesives, and high temperature tapes.

There are three primary requirements for the high resistivity sensor coating 18 and 23. First, the coating itself should not disrupt the process or regression under study while it is regressing. Secondly, the process of applying the high resistivity coatings 18 and 23 to the substrate 14 should be compatible with the substrate 14. Third, the coatings 18 and 23 should not become highly conductive upon burning, thereby creating an electrical short at the tip of the sensor. A further requirement for the high resistivity center coating 18 when the continuous sensor pattern is used is that its resistance does not appreciably change with temperature.

More specifically, the temperature coefficient of resistance (TCR) is a measure of how the resistance of a material changes with its temperature and is defined by the equation:

$$R=R_0+R_0 a'(T-T_0)$$

where
- R=heated resistance (ohms)
- $R_0$=initial resistance (ohms)
- a'=temperature coefficient of resistance, TCR
- T=heated temperature (C)
- $T_0$=initial temperature (C).

A desired property of the high resistive center coating 18 for the continuous sensor is that it have a sufficiently low TCR to avoid the resistance of such layer being affected by temperatures. This, of course, is particularly true in situations where the regression test material is burned as in the fuel grain of a hybrid rocket engine. For material with a relatively high TCR, a change in resistance caused by heat can be misconstrued as a change in the length of the sensor layer, thereby resulting in measurement error. Preferably, the TCR of the sensor layer 18, when used in environments such as the fuel grain of a rocket engine where regression of the test material is caused by burning, should preferably be less than about 100 parts per million per degree centigrade (ppm/C) within the operative temperature range and more preferably less than about 50 ppm/C.

The TCR should be such that the change in resistance over the test should vary no more than about 10%, preferably no more than 5%, and most preferably no more than about 2%. As a result of various testing, it has been determined that a material known as nichrome, an alloy of nickel and chromium, deposited at a thickness of about 50 angstroms and at a sheet resistance of about 100 ohms per square onto a polyester substrate exhibited a sufficiently low TCR for a hybrid rocket engine application. Although nichrome has been found to be one of the preferred materials for use in the particular application of the preferred embodiment, many resistive coatings with extremely low TCRs have been developed. Materials other than nichrome such as various other metal alloys and silver filled conductive inks and glazes can also be used to form the high resistivity sensor layers 18 and 23.

The leads 20 and 21 can be electrically connected to the legs 16 and 17 by a variety of methods. One such method includes forming the connection using a room temperature cured conductive epoxy. Other techniques may also be used such as soldering, parallel gap welding, ultrasonic welding, the use of solder pads, and physical crimp-type connectors 22, among others. Such techniques must, however, be compatible with the substrate material 14, the conductive legs 16 and 17, and the sensor layers 18 and 23. In the preferred embodiment, the conductive legs 16 and 17 have an electrical resistivity with a sheet resistance less than about 1 olms/square and the conductive sensor element 18 has an electrical resistivity with a sheet resistance greater than about 10 ohms/square.

The insulating sensor coating 19 is not required for all applications, however, when required it preferably promotes adhesion between the sensor and the host material. For hybrid rocket fuels and solid propellants, one of the preferred coatings is nitrocellulose, and for some silicone based ablatives one of the preferred coatings is polyester. However, other coatings may be used for these applications. The sensor coating 19 when used should preferably cover both sensor legs 16 and 17, the high resistive sensor elements 18 and 23, and the substrate 14. The sensor coating 19 may be applied by spraying or brushing it on, by dipping the sensor 10 into the coating 19, or by any other approach. Preferably, the coating is dissolved in a solvent or carrier which evaporates and leaves the coating on the sensor 10. It is important that the solvent or carrier does not dissolve or adversely affect the sensor substrate 14 or the conductive sensor elements 16, 17, 18 and 23.

The sensor 10 of the present invention is preferably made by using one of two techniques for applying the electrically conductive elements or coatings 16, 17, 18 and 23 to the substrate. One is to apply the coatings using vapor deposition. This is accomplished by first vapor depositing the high resistivity center coatings 18 or 23 onto the substrate 14. If the ladder sensor pattern (FIGS. 4 and 5) is being made, an appropriate mask can be used to produce the several rungs 23. A mask is then used to apply the proper patterning for the legs 16 and 17, which are vapor deposited in laterally spaced relationship directly onto, and in electrical contact with, the high resistivity coatings 18 or 23. The leads 20 and 21 are then connected to the legs 16 and 17. Several sensor bodies can be made during a single vapor deposition run by using the appropriate masking.

A second technique for applying the electrically conductive coatings is to use electrically conductive inks. This is achieved by first applying the conductive ink of high resistivity sensor coatings 18 or 23 onto the substrate via masking techniques, a computer controlled pen, or other method, and then curing the ink by baking it at a prescribed temperature for a specific period of time, as dictated by the specific ink used. The conductive legs 16 and 17 of the sensor 10 are then applied on top of and in electrical contact with the high resistivity coating 18 and 23 via masking techniques, a computer controlled pen, or other method, and then the ink is cured by baking it at a prescribed temperature for a specific period of time, as dictated by the specific ink used. Other methods may be used for applying or patterning the electrically conductive coatings 16, 17, 18, and 23 onto the substrate 14, including chemical etching.

Figure 6:
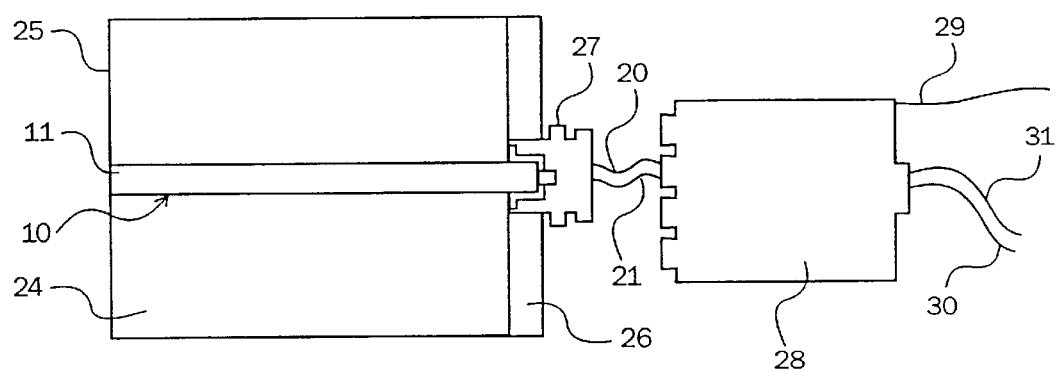
FIG. 6 is a view, partially in section, of a sensor installation using a feed through connector for signal transmission and a unit for processing the sensor signal.
Figure 7:
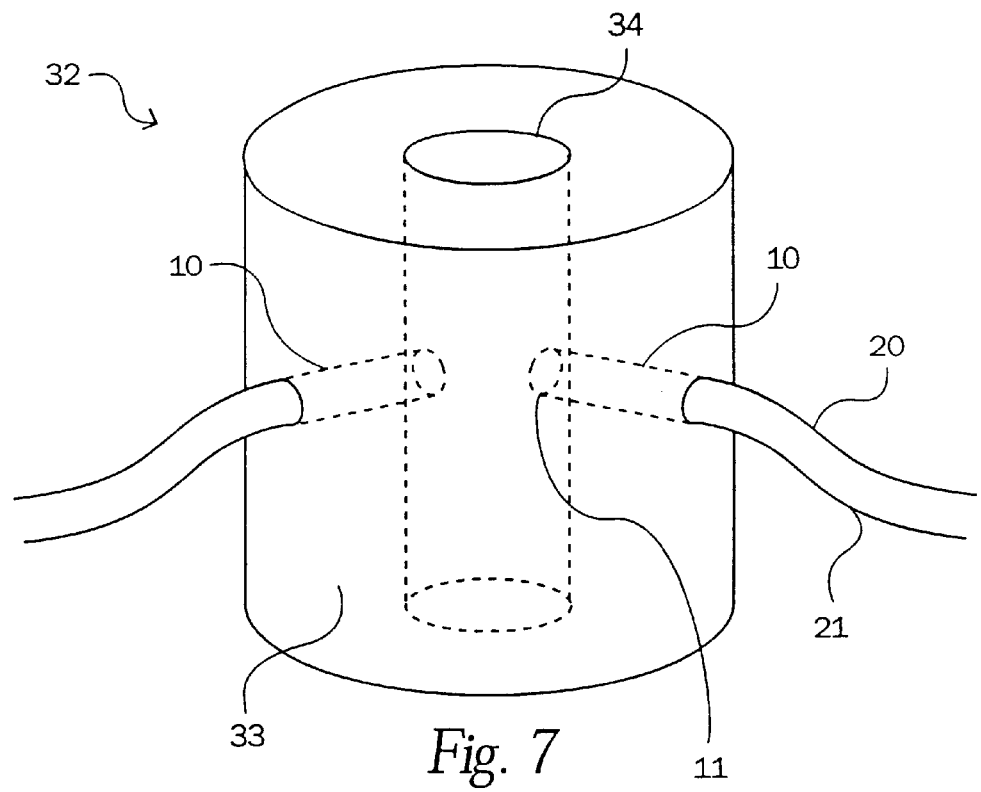
FIG. 7 is an isometric view of a fuel grain for a rocket engine propellant with a plurality of sensors embedded therein.
Figure 8:
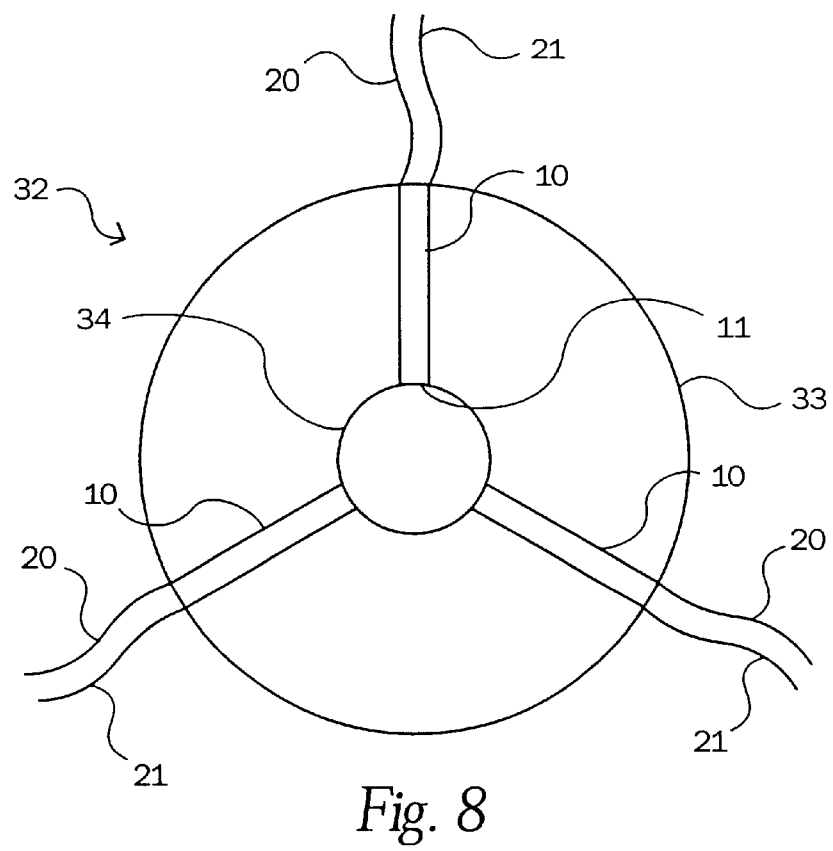
FIG. 8 is a view, partially in section, as viewed along the section line 8—8 of FIG. 7.

The sensor in accordance with the present invention may be cast directly into the test material with the test end 11 exposed to the regression surface such as is shown in FIGS. 6, 7 and 8, or can be inserted into the test material using a slot-type or plug-type installation after the material has been formed or cured. Further, the sensor 10 may be as short as 0.02 inches or less and as long as 12 inches or more. Casting a sensor 10 into a material can be achieved by first accurately positioning the sensor into the material casting mold, and then pouring or packing the material around the sensor 10, and allowing it to cure or harden, if necessary. FIG. 6 shows a sensor 10 installed into a test material 24 having a regressing surface 25. The sensor 10 is positioned such that it is perpendicular to the regressing surface 25 and such that the test end 11 is flush with the regressing surface 25, so that as the surface 25 regresses, the end 11 similarly regresses, thereby shortening the length of the sensor 10. For the continuous sensor pattern, this in turn shortens the length of the center resistive sensor layer 18 (FIG. 2) and results in a change in the sensor resistance as measured from the leads 20 and 21.

For the ladder sensor pattern (FIGS. 4 and 5), the test end 11 of the sensor 10 similarly regresses and causes a step change in the resistance measured from the leads 20 and 21 when the regressing surface causes a rung 23 of the sensor to burn or wear away. In both cases, these changes in resistance can be detected and measured through the use of proper signal conditioning. This measurement can be correlated to the instantaneous material thickness and surface regression as there is a prescribed relationship between the sensor resistance and its instantaneous length.

As an alternative to casting the sensor 10 into the test material, the sensor 10 can be installed into the test material after it has been cured, formed, or otherwise produced in a solid form. Preferably, the first step for this type of installation is to produce a cavity in the test material, into which the sensor shall be inserted. The cavity shall be of the proper orientation to facilitate accurate sensor positioning, as will be described below. The cavity can be formed by casting it into the material, drilling, slicing or otherwise mechanically removing or separating a portion of the material. Next, the sensor is preferably positioned into the material such that the length of the sensor is perpendicular to the direction of the test material surface regression that is to be measured.

Additionally, the test end 11 shall be the closest end of the sensor 10 to the test material regressing surface 25, such as shown in FIG. 6. In the case of a hybrid fuel grain and other applications, a seal between the sensor assembly and the host material must be made to prevent hot, high-pressure gas from penetrating into the fuel grain and disrupting sensor measurements and the operation of the rocket engine. This can be achieved by using uncured fuel, or other material that will eventually cure or harden, to effect a seal between the sensor 10 and the test material. There are many approaches that can be utilized for applying the sealant material. They include injecting the sealant material between the sensor 10 and the test material after positioning the sensor in the test material, and first filling the cavity in the test material with the sealant and then inserting the sensor into the cavity.

An alternate approach to installing a sensor into a test material after it has cured or hardened includes sectioning the test material in half, placing the sensor onto a portion of the surface produced by the sectioning, and gluing or otherwise attaching the two halves back together. Other variations and derivatives of the general concepts described herewith in can be employed for installing sensors into a material after it has cured, hardened, or otherwise been produced in a solid form.

Figure 10:
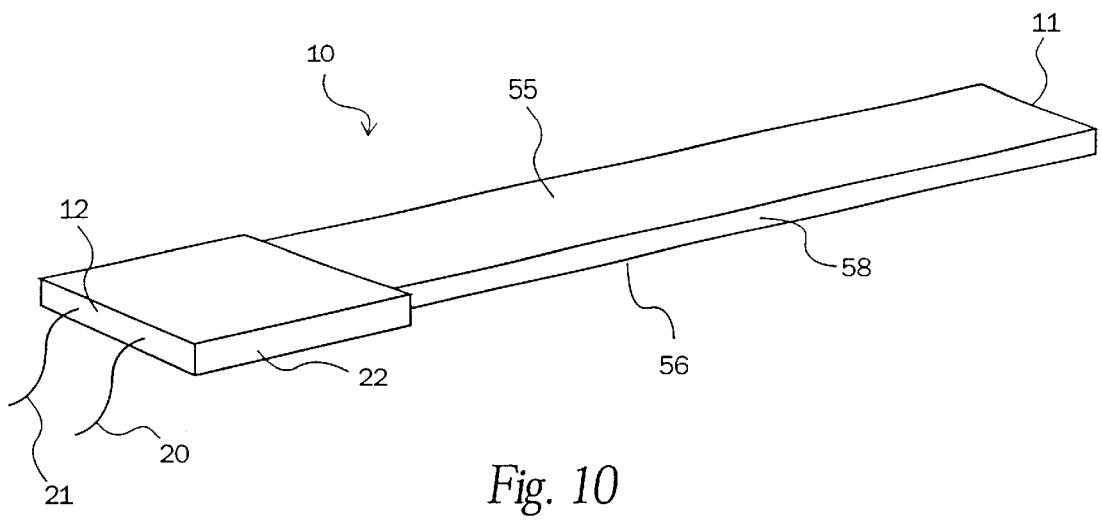
FIG. 10 is an isometric view of a further embodiment of a regression sensor in accordance with the present invention.
Figure 11A:
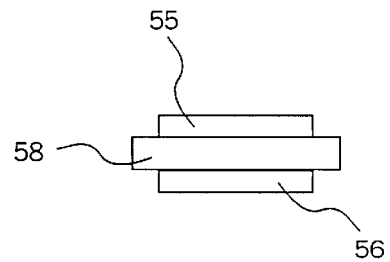
FIG. 11a is a transverse cross-sectional view of an embodiment of FIG. 10 as a sensor with a continuous sensor pattern.
Figure 11B:
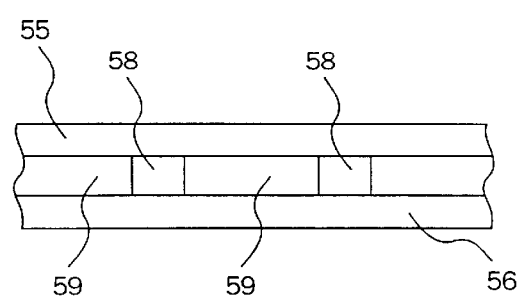
FIG. 11b is a fragmentary longitudinal cross-sectional view of an embodiment of FIG. 10 as a sensor with a ladder sensor pattern.

A further embodiment of a sensor 10 in accordance with the present invention is shown in FIGS. 10, 11a and 11b. In this embodiment, the substrate is essentially eliminated. Thus, the high resistivity element functions both as the high resistivity element as well as the substrate or support for the low resistivity conductive elements. Specifically, in the embodiment of FIGS. 10 and 11, the pair of conductive legs 55 and 56 of low resistivity are provided on opposite sides of a material comprised of the conductive high resistivity element 58. The specific structure is shown best in FIGS. 11a and 11b.

In this embodiment, it is preferred that the high resistivity of element 58 be thick enough to support the low resistivity conductive legs 55 and 56. This embodiment can be provided in the continuous sensor form of FIGS. 1–3 in which the high resistivity element 58 is substantially continuous along the length of the sensor as shown in the cross-sectional embodiment of FIG. 11a. It is contemplated, however, that this embodiment may also be incorporated into the ladder type sensor of FIGS. 4 and 5. This embodiment is shown in the cross-sectional view of FIG. 11b in which a plurality of discrete, high resistivity elements 58 are spaced from each other along the length of the sensor. These spaced elements 58 are separated by areas of electrically insulative material 59.

Figure 9:
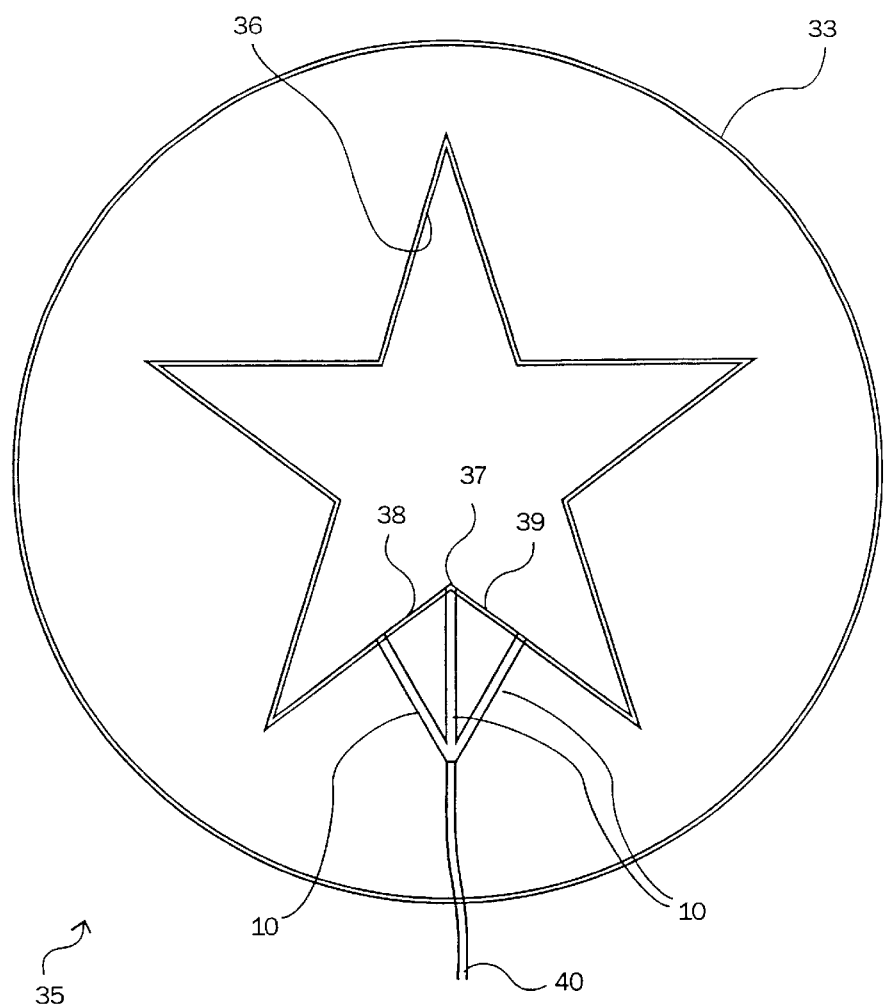
FIG. 9 is a view, partially in section, of a plurality of sensors installed into a solid rocket propellant grain with a star port geometry.

FIGS. 7, 8 and 9 show sensors 10 embedded in various embodiments of the fuel grain 32 of a hybrid rocket motor or a solid rocket propellant. As shown in FIGS. 7 and 8, the fuel grain 32 can be a generally annular structure having a generally cylindrical exterior surface 33 and a generally cylindrical internal, regression surface 34. As shown, the test ends 11 of the sensors 10 extend to the inner regression surface 34. As the fuel grain 32 burns, the regression surface 34 regresses, thereby shortening the length of the sensors 10 as it does so. Again, by applying a voltage to the leads 20 and 21 of each sensor, the change in sensor resistance can be measured, thereby facilitating continuous and instantaneous test material thickness measurement and regression measurement of the surface 34. A cylindrical regression surface 34 is used here in FIGS. 7 and 8 as an example, however, the regression surface 34 can be of any shape and geometry.

In particular, the following regression surface geometries are of specific interest for solid propellants and hybrid fuel grains: star, wagon wheel, lobe, spherical, triangular, and slot. The regression surface of a two or three dimensional surface geometry can be mapped out by using more than one sensor or sensor portion 10 installed into the test material. This is illustrated in FIG. 9 where a composite solid rocket propellant has an internal star port geometry regression surface 36. As shown in FIG. 9, three sensors or sensor portions 10 can be installed into a star port surface geometry 36 to allow the surface regression of an inner star point 37 and adjacent regressing surfaces 38 and 39 to be measured. The local regression at each individual sensor can measured by applying a constant voltage to the individual sensor leads 20 and 21, shown as a bundle of six wires 40 for the three sensors 10, and measuring the resulting current flow.

Figure 12:
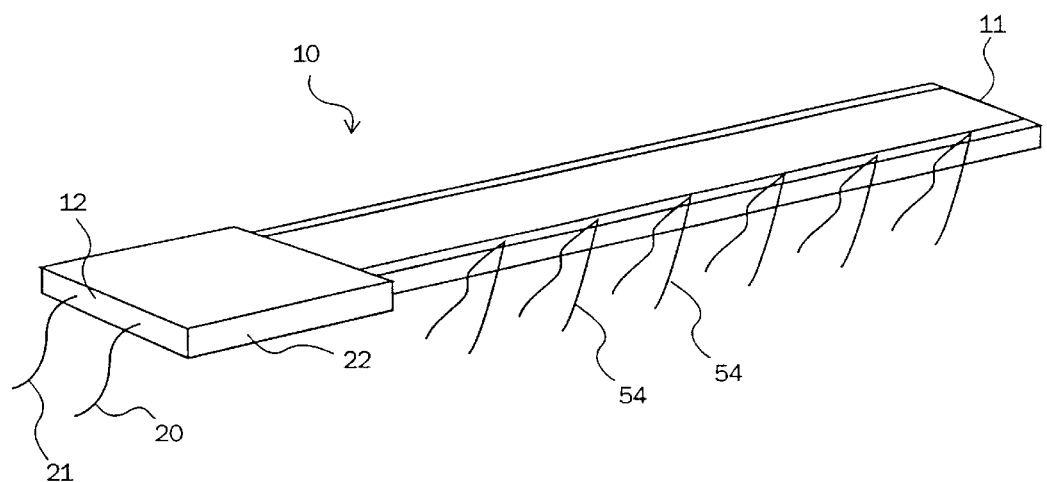
FIG. 12 is an isometric view of an embodiment of a regression sensor with temperature measurement capability.

A further embodiment of the sensor of the present invention is for use in combination with means for measuring temperatures along the sensor and thus providing temperature profile and heat flux measurements. This can be achieved by attaching an individual or plurality of thermocouples, thermistors, resistance temperature devices (RTDs), or other temperature measurement instrumentation, onto known locations along the length of the sensor (either continuous or ladder). An example of this structure is shown in FIG. 12 in which a plurality of thermocouples 54 are spaced along the length of the sensor.

The ladder sensor pattern (FIGS. 4 and 5) can also be used to measure temperature profiles and heat flux in the test material. This can be achieved by providing temperature sensitive elements such as those identified above along the length of the sensor similar to that shown in FIG. 12 or by using resistive materials that are designed to have a known TCR as a function of temperature for the rungs 23 of the ladder sensor 10. In such a structure, as an individual rung 23 of the sensor is being heated, it will change in resistance. This change in resistance can be detected and measured by applying a constant voltage to the leadwires 20 and 21 and measuring the resulting current flow through the sensor. With this embodiment, it is preferable for the sensor rungs 23 to be spaced far enough apart such that only one of the rungs 23 is appreciably rising in temperature at any given time. If this condition is met, then the known TCR of the resistive rung 23 material can be used along with the measured change in sensor resistance to determine the temperature of the rung 23. In this way, the ladder sensor can be used to measure both temperature and regression at the same time.

This temperature measurement feature of the ladder sensor 10 can be used in a hybrid rocket solid fuel grain. In this case, a temperature gradient will be formed in the test material due to heat conduction from the combustion process occurring in the grain port. The sensor rung 23 closest to the test end 11 of the sensor and regression surface 34 will be rising in temperature as the regression surface approaches the rung 23, until the rung 23 is consumed. As stated above, the rungs 23 are preferably spaced far enough apart such that the temperature gradient in the test material does not appreciably heat up the next adjacent rung 23 from the regressing surface 34.

Figure 13:
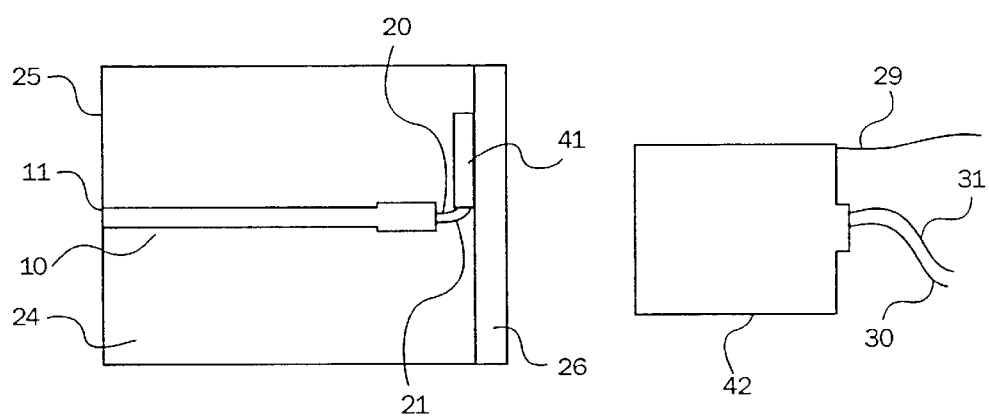
FIG. 13 is a view, partially in section, of a sensor installed in a test material which uses wireless data transmission to send sensor data to a remote receiver.

With reference to FIGS. 6 and 13, there are several general approaches that can be used to transmit sensor data from an enclosed, high pressure, high temperature, or other environment, to the ambient or other external environment. FIG. 6 shows the use of a wire feedthrough connector 27 to guide the sensor leads 20 and 21 out of the engine while providing a pressure tight seal around the wires. The feedthrough connector 27 is attached to the pressure vessel 26 which separates the test environment from the ambient environment. The leads 20 and 21 are then electrically connected to a signal processing unit 28 which converts the sensor resistance into a signal which can be correlated to the sensors 10 instantaneous length. A pair of processed signal leads 30 and 31 extend from the signal processing unit 28. These leads 30 and 31 reflect the active sensor length and thus the extent to which the surface 25 has regressed. Standard 110 volt AC power can be supplied to the signal processing unit via a power cord 29.

An alternate approach to transmitting a signal from inside a high pressure or other environment to a different environment is remote data transmission. FIG. 13 illustrates this approach, where a signal processing unit 41 is placed inside of the test environment. The sensor leads 20 and 21 are electrically connected to the signal processing unit 41. The signal processing unit 41 transmits a signal from inside the test environment to an external receiver 42. The receiver 42 accepts the signal from the signal processing unit 41 and produces another signal on leads 30 and 31 which reflects the active sensor length and thus the extent to which the surface 25 has regressed. This remote data transmission technique eliminates the need to produce penetrations in the pressure vessel 26 which has particular utility for ground based testing of flight hardware or on board actual flight systems.

A still further alternate means of obtaining the regression data is to use a miniature signal conditioner and data recorder installed inside of the pressure vessel which would continuously read and store the regression data during the test. The recorder could then be retrieved after the test or process has been completed, allowing the data to be collected. This approach eliminates the need to produce penetrations in the pressure vessel for data acquisition.

Figure 14:
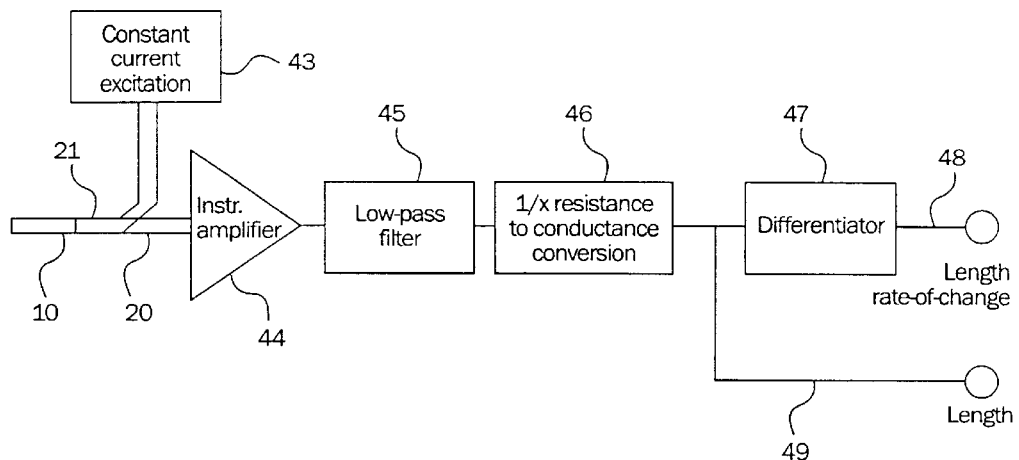
FIG. 14 is a schematic diagram of one embodiment of a signal conditioner for the regression sensor of the present invention.
Figure 15:
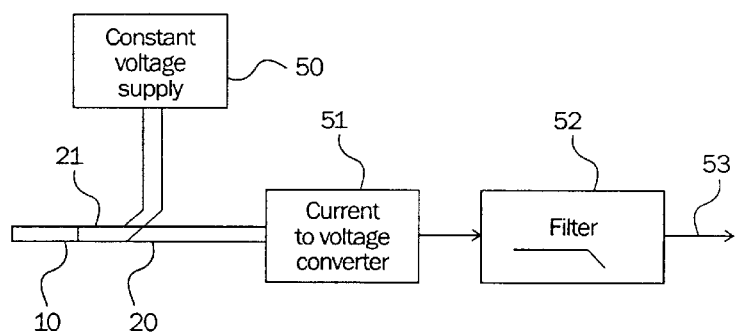
FIG. 15 is a schematic diagram of a further embodiment of a signal conditioner for the sensor of the present invention.

FIGS. 14 and 15 are schematic diagrams of the sensor circuitry used to measure instantaneous surface regression using the sensor as described above. In the embodiment of FIG. 14, a constant current from a current supply 43 is applied to the sensor 10 via the sensor leads 20 and 21. The resulting voltage drop across the sensor 10 is conditioned by sending it through an amplifier 44, a low pass filter 45, a resistance to conductance conversion means 46 and finally through a differentiator 47. The resulting output signal 48 is related to the instantaneous test material surface regression rate. The output signal 49 after the resistance to conductance conversion is related to the instantaneous test material thickness.

An alternate signal conditioner for the sensor output is shown in FIG. 15. In this embodiment, a constant voltage from a voltage supply 50 is applied across the sensor via the sensor leads 20 and 21. The resulting current through the sensor 10 is then conditioned by sending it through a current to voltage converter 51 which transforms the current into a voltage that is proportional to the sensors 10 instantaneous conductance. The output from the converter 51 is then directed to a low pass filter 52, with the output 53 being measured to determine the length of the sensor and thus the regression of the test material. The differentiator 47 shown in FIG. 14 can also be used with the constant voltage signal conditioning approach to provide a signal related to the instantaneous surface regression rate of the test material.

Although the description of the preferred embodiment has been quite specific, it is contemplated that various modifications can be made without deviating from the spirit of the present invention. Accordingly, it is intended that the scope of the present invention can be dictated by the appended claims rather than by the description of the preferred embodiment.

What is claimed is:

1. A material regression sensor comprising:
    first and second electrically conductive legs, said conductive legs being spaced from one another and each having a test end, a measurement end and a length extending between said test end and said measurement end;
    an electrically conductive sensor element positioned between, and being electrically connected with, said first and second conductive legs, said conductive sensor element extending along at least a portion of the length of said first and second conductive legs; and
    first and second measurement leads electrically connected respectively with said first and second legs.

2. The material regression sensor of claim 1 wherein each of said first and second legs and said conductive sensor element has an electrical resistivity and wherein the electrical resistivity of said first and second legs is lower than the electrical resistivity of said conductive sensor element.

3. The material regression sensor of claim 2 wherein said first and second legs have an electrical resistivity with a sheet resistance less than about 1 ohms/square and said conductive sensor element has an electrical resistivity with a sheet resistance greater than about 10 ohms/square.

4. The material regression sensor of claim 1 including a substrate supporting said first and second electrically conductive legs and said conductive sensor element.

5. The material regression sensor of claim 4 wherein a portion of said conductive sensor element is positioned between said substrate and said first and second electronically conductive legs.

6. The material regression sensor of claim 4 wherein said substrate is constructed of polyester or celluloid.

7. The material regression sensor of claim 1 including means for applying one of an electrical voltage or current to said first and second conductive legs.

8. The material regression sensor of claim 7 including a signal transmitter for transmitting a signal reflecting the current or voltage across said first and second conductive legs to a remote location.

9. The material regression sensor of claim 1 wherein said conductive sensor element is substantially continuous throughout its length.

10. The material regression sensor of claim 1 wherein said conductive sensor element comprises a plurality of conductive sensor element portions spaced from one another along the length of said first and second conductive legs.

11. The material regression sensor of claim 10 wherein at least two of said plurality of conductive sensor element portions are constructed of materials having a known temperature coefficient of resistance (TCR).

12. The material regression sensor of claim 1 wherein said conductive sensor element includes first and second surfaces and wherein said first and second electrically conductive legs are supported by said first and second surfaces, respectively.

13. The material regression sensor of claim 1 including one or more temperature sensing elements positioned along the length of the sensor.

14. The material regression sensor of claim 1 wherein said first and second electrically conductive legs are substantially equally spaced from one another along the length of said legs.

15. The material regression sensor of claim 1 including a non-conductive coating covering said first and second electrically conductive legs and said conductive sensor element.

16. The material regression sensor of claim 15 wherein said non-conductive coating is a nitrocellulose material.

17. The material regression sensor of claim 15 further including a substrate supporting said first and second electrically conductive legs and said conductive sensor element and a non-conductive exterior coating.

18. The material regression sensor of claim 1 embedded in a regression material.

19. The material regression sensor of claim 18 wherein said regression material is one of a solid fuel, solid oxidizer, solid rocket propellant, ablative nozzle, thermal protection material, vehicle tire and brake pad.

20. A method of measuring the regression of a material having a regression surface comprising:

providing a sensor having a pair of spaced electrically conductive legs each having a test end, a measurement end and a length between said test and said measurement end, an electrically conductive sensor element positioned between said pair of legs and extending along at least a portion of the length of said first and second legs between their test and measurement ends and a pair of measurement leads electrically connected to said pair of legs;

embedding said sensor in said material with said test end of each of said legs extending toward said regression surface;

applying a measurement voltage or current to said leads.

21. A test material and material regression sensor incorporated therein for measuring the surface regression of a surface of said test material comprising:

a test material having a regression surface; and a material regression sensor embedded in said test material wherein said sensor includes;

first and second spaced electrically conductive legs, each of said first and second legs having a test end and an opposite end and being oriented in said test material with their test end extending toward said regression surface, an electrically conductive sensor element having a portion positioned between said first and second legs at a point between said test and opposite ends of said legs said conductive sensor element extending at along least a portion of the length of said first and second conductive lengths.

22. A test material and material regression sensor of claim 21 wherein regression of regression surface results in regression of a portion of said first and second legs from their test ends toward their opposite ends and regression of a portion of said sensor element.

23. A test material and material regression sensor of claim 21 wherein said first and second legs are substantially perpendicular to said regression surface.

24. A test material and material regression sensor of claim 21 including embedding said sensor in said material so that regression of the material from said regression surface results in regression of a portion of said sensor element.

25. The method of claim 24 wherein said regression of a portion or said sensor element occurs along said pair of legs.

* * * * *